US010551357B2

(12) United States Patent
Murray et al.

(10) Patent No.: US 10,551,357 B2
(45) Date of Patent: Feb. 4, 2020

(54) HIGH RESOLUTION PHOTOACOUSTIC IMAGING IN SCATTERING MEDIA USING STRUCTURED ILLUMINATION

(71) Applicant: THE REGENTS OF THE UNIVERSITY OF COLORADO, Denver, CO (US)

(72) Inventors: Todd W. Murray, Golden, CO (US); Peter Burgholzer, Gallneukirchen (AT); Markus Haltmeier, Innsbruck (AT)

(73) Assignees: The Regents of the University of Colorado, a body corporate, Denver, CO (US); Research Center for Non Destructive Testing GmbH, Linz (AT); University of Innsbruck, Innsbruck (AT)

(*) Notice: Subject to any disclaimer, the term of this patent is extended or adjusted under 35 U.S.C. 154(b) by 0 days.

(21) Appl. No.: 16/337,339

(22) PCT Filed: Sep. 28, 2017

(86) PCT No.: PCT/US2017/054133
§ 371 (c)(1),
(2) Date: Mar. 27, 2019

(87) PCT Pub. No.: WO2018/064397
PCT Pub. Date: Apr. 5, 2018

(65) Prior Publication Data
US 2019/0234911 A1    Aug. 1, 2019

Related U.S. Application Data

(60) Provisional application No. 62/400,685, filed on Sep. 28, 2016.

(51) Int. Cl.
*G01N 29/44*    (2006.01)
*G01N 29/24*    (2006.01)
(Continued)

(52) U.S. Cl.
CPC ..... *G01N 29/4472* (2013.01); *G01N 21/1702* (2013.01); *G01N 21/4795* (2013.01);
(Continued)

(58) Field of Classification Search
CPC .................. G01N 29/4472; G01N 29/2418
(Continued)

(56) References Cited

U.S. PATENT DOCUMENTS

2009/0118622 A1* 5/2009 Durkin ................ A61B 5/0073
                                                            600/473
2012/0022381 A1   1/2012 Tearney et al.
(Continued)

FOREIGN PATENT DOCUMENTS

WO    2011/035408 A1    3/2011
WO    2015/031395 A1    3/2015
(Continued)

OTHER PUBLICATIONS

Hojman, et al. "Photoacoustic imaging beyond the acoustic diffraction-limit with dynamic speckle illumination and sparse joint support recovery", Optics Express vol. 25, Issue 5, pp. 4875-4886 (2017) 13 pgs.
(Continued)

*Primary Examiner* — Tarun Sinha
(74) *Attorney, Agent, or Firm* — Maschoff Brennan; Paul G. Johnson

(57) ABSTRACT

A method for high resolution photoacoustic imaging in scattering media using structured illumination may include illuminating a sample of an absorption object with structured illumination, including illuminating the sample with multiple different speckle patterns at different times. The method may also include detecting multiple photoacoustic signals generated by the absorption object in response to illumination with the different speckle patterns to generate multiple
(Continued)

photoacoustic responses. The method may also include reconstructing an absorber distribution of the absorption object by exploiting joint sparsity of sound sources in the plurality of photoacoustic responses.

22 Claims, 9 Drawing Sheets

(51) Int. Cl.
| | | |
|---|---|---|
| G01N 21/17 | (2006.01) | |
| G01N 29/06 | (2006.01) | |
| G01N 21/47 | (2006.01) | |
| G01N 29/00 | (2006.01) | |
| G01N 21/84 | (2006.01) | |

(52) U.S. Cl.
CPC ......... *G01N 29/00* (2013.01); *G01N 29/0672* (2013.01); *G01N 29/2418* (2013.01); *G01N 2021/1706* (2013.01); *G01N 2021/479* (2013.01); *G01N 2021/8444* (2013.01); *G01N 2201/106* (2013.01)

(58) Field of Classification Search
USPC .......................................................... 73/602
See application file for complete search history.

(56) References Cited

U.S. PATENT DOCUMENTS

2012/0236310 A1* 9/2012 Lesage ................. A61B 5/0073
356/432
2014/0360271 A1* 12/2014 Fukutani ............ G01N 29/0654
73/602
2016/0338623 A1* 11/2016 Tholl ................... A61B 5/1455

FOREIGN PATENT DOCUMENTS

WO 2016/054067 A1 4/2016
WO 2018/064397 4/2018

OTHER PUBLICATIONS

Chaigne, et al. "Super-resolution photoacoustic fluctuation imaging with multiple speckle illumination", Optica vol. 3, Issue 1, pp. 54-57 (2016) 10 pgs.
International Search Report and Written Opinion, PCT/US2017/054133, dated Dec. 14, 2017, 7 pgs.

* cited by examiner

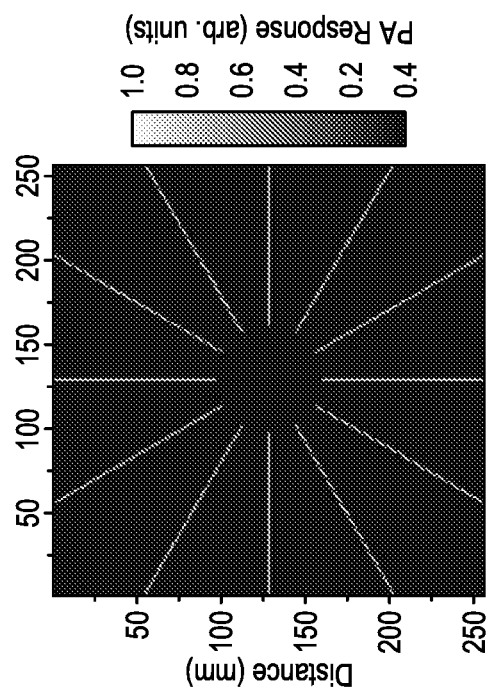
FIG. 4A Object
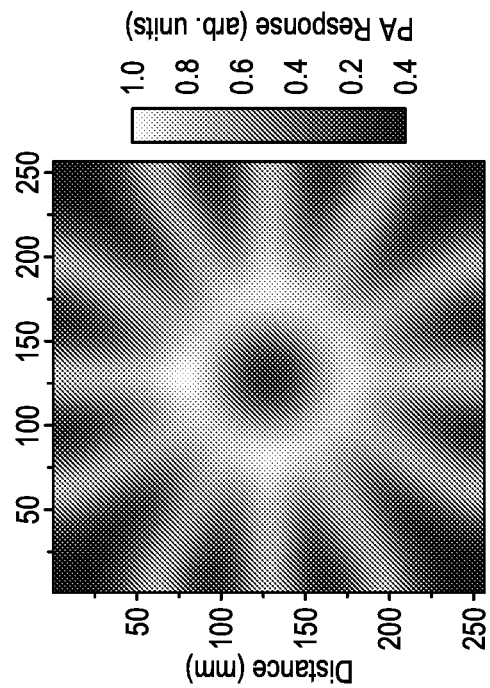
FIG. 4B Mean
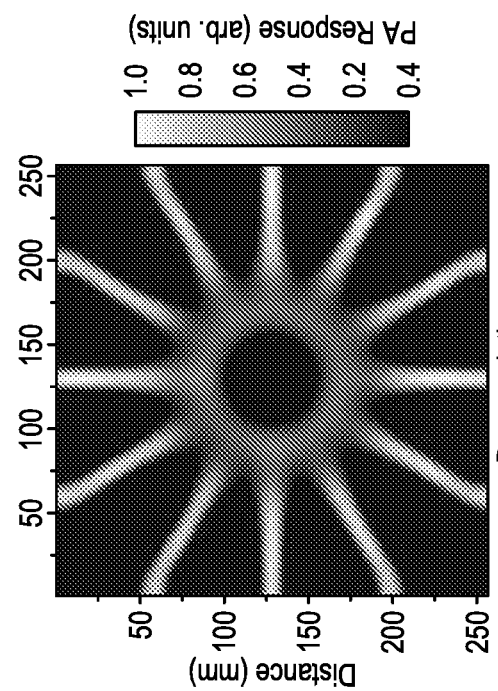
FIG. 4C Deconvolution
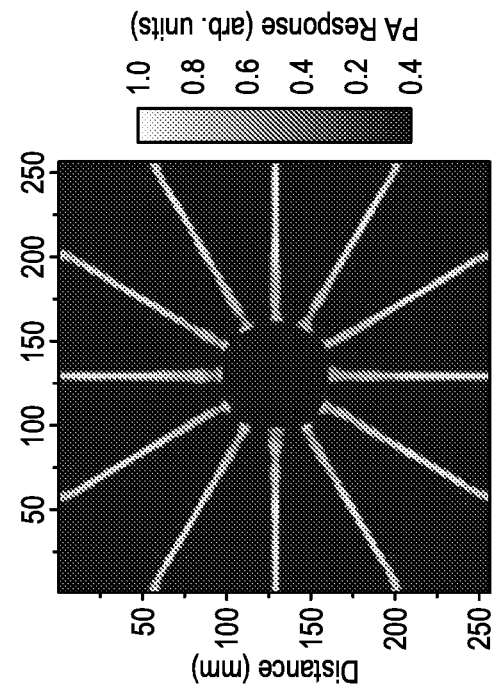
FIG. 4D BSIPAM

HIGH RESOLUTION PHOTOACOUSTIC IMAGING IN SCATTERING MEDIA USING STRUCTURED ILLUMINATION

CROSS-REFERENCE TO RELATED APPLICATION

This PCT Patent Application claims priority pursuant to 35 U.S.C. § 119(e) to U.S. Provisional Application No. 62/400,685, entitled "HIGH RESOLUTION PHOTOACOUSTIC IMAGING IN SCATTERING MEDIA USING STRUCTURED ILLUMINATION", filed Sep. 28, 2016, which is hereby incorporated herein by reference in its entirety and made part of the present PCT Patent Application for all purposes.

FIELD

Some embodiments relate to high resolution photoacoustic imaging in scattering media using structured illumination.

BACKGROUND

Unless otherwise indicated herein, the materials described herein are not prior art to the claims in the present application and are not admitted to be prior art by inclusion in this section.

Optical imaging of objects inside or behind turbid media is a challenging endeavor, for example, because multiple scattering scrambles the object information and hides features from view. While techniques such as optical coherence tomography and multiphoton microscopy have been developed to extract ballistic light from scattered light, thus enabling diffraction limited imaging, these approaches are only suitable for imaging depths on the order of five times the scattering mean free path, beyond which the ballistic photon population is too weak with respect to the scattered light to provide useful information.

The subject matter claimed herein is not limited to embodiments that solve any disadvantages or that operate only in environments such as those described above. Rather, this background is only provided to illustrate one example technology area where some embodiments described herein may be practiced.

SUMMARY

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter. A method is disclosed for high resolution photoacoustic imaging in scattering media using structured illumination. The method may include illuminating a sample of an absorption object with structured illumination, including illuminating the sample with multiple different speckle patterns at different times. The method may also include detecting multiple photoacoustic signals generated by the absorption object in response to illumination with the different speckle patterns to generate multiple photoacoustic responses. The method may also include reconstructing an absorber distribution of the absorption object by exploiting joint sparsity of sound sources in the plurality of photoacoustic responses.

In some embodiments, reconstructing the absorber distribution of the absorption object by exploiting joint sparsity of sound sources in the photoacoustic responses includes minimizing a sum of a smooth data fitting term f(p) and a non-smooth but convex regularization term $g_{\alpha_1,\alpha_2}(p)$.

In some embodiments, the smooth data fitting term f(p) depends on a point spread function (PSF) or a line spread function (LSF) of an ultrasound transducer that detects the photoacoustic signals and on the sound sources in the photoacoustic responses; the convex regularization term $g_{\alpha_1,\alpha_2}(p)$ depends on an $\ell^1$-norm and $\ell^2$-norms of pixel values over all blocks; the $\ell^1$-norm accounts for sparsity; and an inner one of the $\ell^2$-norms couples together different sound sources that represent the same absorption object in different ones of the plurality of photoacoustic responses.

In some embodiments, minimizing the sum of the smooth data fitting term f(p) and the non-smooth but convex regularization term $g_{\alpha_1,\alpha_2}(p)$ includes minimizing the sum of the smooth data fitting term $f(p) \triangleq \sum_{m=1}^{M} \sum_{n=1}^{N} |h * p_m(x_i)|^2$ and the non-smooth but convex regularization term $$g_{\alpha_1,\alpha_2}(p) = \alpha_1 \|p\|_{2,1} + \frac{\alpha_2}{2} \|p\|_2^2.$$

In some embodiments, M is a number of the photoacoustic responses, N is a number of data points that make up each of the photoacoustic responses, h is a PSF or a LSF of an ultrasound transducer that detects the photoacoustic signals, and $p_m(x_i)$ is a sound source in an mth one of the photoacoustic responses at each data point $x_i$.

In some embodiments, minimizing the sum of the smooth data fitting term f(p) and the non-smooth but convex regularization term $g_{\alpha_1,\alpha_2}(p)$ includes minimizing the sum of the smooth data fitting term f(p) and the non-smooth but convex regularization term $g_{\alpha_1,\alpha_2}(p)$ using a block-fast iterative threshold algorithm (block-FISTA).

In some embodiments, minimizing the sum of the smooth data fitting term f(p) and the non-smooth but convex regularization term $g_{\alpha_1,\alpha_2}(p)$ using the block-FISTA includes performing a gradient step for the smooth data fitting term f(p) and performing a proximal step for the non-smooth but convex regularization term $g_{\alpha_1,\alpha_2}(p)$.

In some embodiments, performing the proximal step includes performing a soft-thresholding operation.

In some embodiments, minimizing the sum of the smooth data fitting term f(p) and the non-smooth but convex regularization term $g_{\alpha_1,\alpha_2}(p)$ using the block-FISTA includes: determining an arbitrary value $p^{(0)}$ for the absorber distribution $p^{(k)}$; selecting a sequence of step sizes $\{sk\}$; determining initial values $z^{(0)}=p^{(0)}$ and $t0=1$; setting an integer increment value, k, to k=1; and calculating tk, z(k), and/or p(k) according to:

$$p^{(k)} = \mathbb{T}_{s\alpha_1,s\alpha_2}(z^{(k-1)} - s(h * [y_m - h * z_m^{(k-1)}])_{m=1,\ldots,M}),$$

$$t_k = \frac{1 + \sqrt{1 + 4t_{k-1}^2}}{2}, \text{ and}$$

$$z^{(k)} = p^{(k)} + \frac{t_{k-1} - 1}{t_k}(p^{(k)} - p^{(k-1)}).$$

A non-transitory computer-readable medium is disclosed that has computer-readable instructions stored thereon that are executable by a processor to perform a method for high resolution photoacoustic imaging in scattering media using structured illumination. The method may include illuminating a sample of an absorption object with structured illumination, including illuminating the sample with multiple different speckle patterns at different times. The method may also include detecting multiple photoacoustic signals generated by the absorption object in response to illumination with the different speckle patterns to generate multiple photoacoustic responses. The method may also include reconstructing an absorber distribution of the absorption object by exploiting joint sparsity of sound sources in the plurality of photoacoustic responses.

An apparatus is disclosed that may include a light source, an optical train, and an ultrasound transducer. The optical train may be configured to focus light from the light source as structured illumination onto a sample that includes an absorption object, where the structured light includes multiple different speckle patterns focused on the sample at multiple different times. The ultrasound transducer may be configured to generate multiple photoacoustic responses of multiple photoacoustic signals generated by the absorption object in response to illumination with the different speckle patterns. The ultrasound transducer may have a PSF or a LSF. The processor may be configured to perform operations that include reconstructing an absorber distribution of the absorption object by exploiting joint sparsity of sound sources in the photoacoustic responses using the PSF or LSF of the ultrasound transducer.

In some embodiments, the light source is configured to emit pulses of an illumination beam toward the sample. Each pulse that reaches the sample may have a different speckle pattern than other pulses.

In some embodiments, the optical train may include a diffuser located in an optical path between the light source and the sample. In some embodiments, the optical train may include a dynamic scattering media such as biological tissue. When light propagates through biological tissue, it may generate a speckle pattern. This speckle pattern may change rapidly due to physiological motion.

In some embodiments, the apparatus may further include a motorized scanning stage configured to rotate the diffuser about an axis parallel to a direction of travel of the light through the diffuser between an end of one pulse and a beginning of a next pulse to modify the structured illumination to have a different speckle pattern at the sample from one pulse to the next.

In some embodiments, the optical train further includes: an adjustable aperture located in the optical path between the diffuser and the sample; and a lens located in the optical path between the adjustable aperture and the sample. A speckle size of the different speckle patterns of the structured illumination may depend on a center wavelength of the light, a focal length of the lens, and a diameter of the adjustable aperture.

In some embodiments, a spatial resolution of the absorber distribution is within a range of one to two times the speckle size.

In some embodiments, a spatial resolution of the absorber distribution is limited by the speckle size rather than the LSF or PSF of the ultrasound transducer.

In some embodiments, reconstructing the absorber distribution of the absorption object by exploiting joint sparsity of sound sources in the photoacoustic responses includes minimizing a sum of a smooth data fitting term f(p) and a non-smooth but convex regularization term $g_{\alpha_1,\alpha_2}(p)$.

In some embodiments, minimizing the sum of the smooth data fitting term f(p) and the non-smooth but convex regularization term $g_{\alpha_1,\alpha_2}(p)$ includes minimizing the sum of the smooth data fitting term f(p) and the non-smooth but convex regularization term $g_{\alpha_1,\alpha_2}(p)$ using a block-FISTA.

In some embodiments, minimizing the sum of the smooth data fitting term f(p) and the non-smooth but convex regularization term $g_{\alpha_1,\alpha_2}(p)$ using the block-FISTA includes performing a gradient step for the smooth data fitting term f(p) and performing a proximal step for the non-smooth but convex regularization term $g_{\alpha_1,\alpha_2}(p)$.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

A further understanding of the nature and advantages of the present invention may be realized by reference to the remaining portions of the specification and the drawings wherein like reference labels are used throughout the several drawings to refer to similar components. In some instances, reference labels include a numerical portion followed by a latin-letter suffix; reference to only the numerical portion of reference labels is intended to refer collectively to all reference labels that have that numerical portion but different latin-letter suffices. The invention will be described and explained with additional specificity and detail through the use of the accompanying drawing, in which:

FIG. 4A illustrates an example simulated absorber distribution of an example star-shaped absorbing object.

FIG. 4B illustrates a simulated mean image of the absorbing object of FIG. 4A.

FIG. 4C illustrates a simulated deconvolution image of the absorbing object of FIG. 4A.

FIG. 4D illustrates a simulated blind structured illumination photoacoustic microscopy (BSIPAM) image of the absorbing object of FIG. 4A.

DETAILED DESCRIPTION OF SOME EXAMPLE EMBODIMENTS

Systems and methods are disclosed for enhancing the spatial resolution of optical absorption based photoacoustic imaging through or within highly scattering media. The optical speckle pattern that emerges as light propagates through diffuse media provides structured illumination to an object placed behind a scattering wall. The photoacoustic signal produced by such illumination may be detected using an ultrasound transducer. In some embodiments, acquiring multiple photoacoustic images, each produced by a different random and unknown speckle pattern, an image of an absorbing object can be reconstructed with a spatial resolution far exceeding that of the ultrasound transducer. These and other embodiments may exploit joint sparsity and may be valuable for biomedical applications and other fields where high frequency structural information is scrambled by diffusive processes.

As already mentioned, optical imaging of objects inside or behind turbid media is a challenging endeavor, for example, because multiple scattering scrambles the object information and hides features from view. While techniques such as optical coherence tomography and multiphoton microscopy have been developed to extract ballistic light from scattered light, thus enabling diffraction limited imaging, these approaches are only suitable for imaging depths on the order of five times the scattering mean free path, beyond which the ballistic photon population is too weak with respect to the scattered light to provide useful information.

Recently, there have been significant developments in wave front shaping techniques that use scattered light to image objects in turbid media. Here, light is manipulated using a spatial light modulator or nonlinear optical crystal such that scattering is compensated. If the transmission matrix of the sample is unknown, as is often the case in dynamic scattering media, focusing and imaging using wave front may include a feedback signal to guide the optical field to a given location. Noninvasive feedback approaches have been developed that combine optics with acoustics; exploiting either acousto-optic interactions, where an ultrasound field is used to frequency modulate light in the interaction region, or the photoacoustic effect, where the intensity of light at a given location is inferred by the photoacoustic signal amplitude. Wave front shaping in living tissue is also complicated by the fact that it may be required to be done very quickly, as the speckle decorrelation time may be on the order of milliseconds. While techniques for rapid wave front correction continue to evolve, imaging approaches that eliminate the need for implicit or explicit determination of the transmission matrix and wave front correction may prove advantageous both in terms of reducing system complexity and potentially increasing speed.

Figure 1:
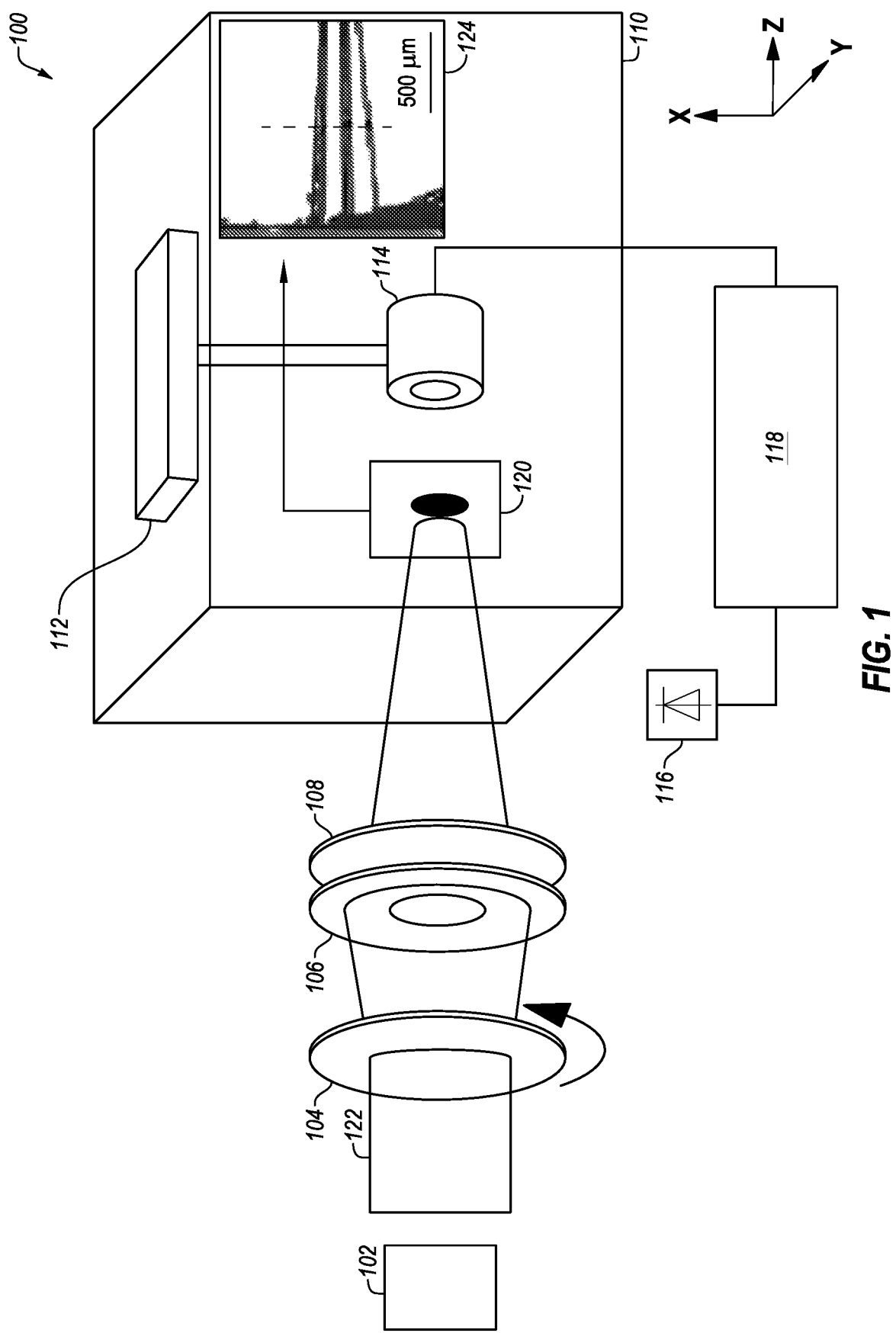
FIG. 1 is a schematic of an example photoacoustic system for high resolution photoacoustic imaging in scattering media using structured illumination.

Some embodiments disclosed herein may include a feedback-free imaging method that uses random optical speckle patterns that naturally emerge as light propagates through strongly scattering media as a structured illumination source for photoacoustic imaging (see e.g., FIG. 1). In some embodiments, blind structured illumination photoacoustic microscopy (BSIPAM) can be used in the multiple scattering domain using photoacoustics, with each of the speckle patterns serving to generate ultrasound which may be detected by a focused transducer.

In some implementations of structured illumination microscopy, resolution enhancement may be limited to about a factor of two because a maximum spatial frequency of an illumination pattern may be constrained by an optical transfer function of the microscope. In some implementations of BSIPAM as described herein, however, the resolution enhancement can potentially be higher than a factor of two and/or higher than the resolution enhancement in known structured illumination microscopy.

The lateral resolution in conventional acoustic-resolution photoacoustic microscopy at depth in scattering media may be determined by the PSF of the transducer. In some embodiments, structured illumination of an object can be considered using a speckle pattern, the maximum spatial frequency in the illumination pattern may be dictated by the speckle size of the speckle pattern and can be well beyond that typically accessible by the transducer. However, by structuring the illumination, the high spatial frequencies in the object may be downshifted into the transducer passband with the resolution of BSIPAM according to some embodiments limited by the speckle size rather than the PSF of the transducer. In some embodiments, a new reconstruction algorithm named block-FISTA can be used to account for the unknown speckle patterns. In some embodiments, the block-FISTA can exploit joint sparsity constraints and/or the fact that all speckle patterns illuminate the same absorber distribution.

Some embodiments may recover the absorber distribution p at a spatial resolution close to the speckle size, e.g., at a resolution within a range of one to two times the speckle size. Suppose that M different speckle patterns $\Phi_1, \Phi_2, \ldots, \Phi_M$ may be used. After proper discretization it can be assumed that the speckle patterns and the absorber distribution are represented by discrete vectors $\Phi_m, p \in \mathbb{R}^N$, where the components denote values at equidistant points $x_i$ in the imaging domain. The measured PA data are then given by:

$$y_m = h^*[\Phi_m \cdot p] + \epsilon_m \text{ for } m=1, \ldots, M \quad (1)$$

Here $h \in \mathbb{R}^N$ for example, may denote the LSF or PSF of the PA imaging system (in discrete form), $[a \cdot b](x_i) \triangleq a(x_i)b(x_i)$ is the point-wise multiplication, $[a^*b](x_i) \triangleq \Sigma a(x_i - x_j)b(x_j)$ is the convolution operation, and $\epsilon_m$ indicates the noise (error) in the data. In some embodiments, the goal is to recover the absorber distribution and, to some extent, the speckle pattern $\Phi_m$ from the data in the above equation. The product $\Phi_m \cdot p$ is the sound source corresponding to the m-th speckle pattern. Because the intensity distribution and the speckle patterns are unknown, the system may include MN equations for (M+1)N unknown scalar parameters and therefore is underdetermined. On the other hand, the sound sources $p_m \triangleq \Phi_m \cdot \rho$ may be uniquely determined by the deconvolution equations $y_m = h * p_m + \epsilon_m$ for $m = 1, \ldots, M$. However, due to the ill-conditioned nature of deconvolution with a smooth kernel, these uncoupled equations are sensitive to errors and further only provide low-resolution reconstructions when solved independently and/or without proper regularization. In some embodiments, there may be a block-sparsity penalty to obtain high-resolution reconstructions.

In some embodiments, the exploitation of sparsity may allow for super-resolution signal recovery. A naive approach incorporating sparsity, for example, would be to look, separately, for the sparsest solution of any individual equation $y_m = h * p_m + \epsilon_m$. However such an approach still misses the main feature of the reconstruction problem, namely that all products $p_m = \Phi_m \cdot \rho$ come from the same density distribution $\rho$. Such a joint-sparsity (or block-sparsity) situation can be implemented by using the joint sparsity term:

$$\|p\|_{2,1} = \sum_{i=1}^{N} \sqrt{\sum_{m=1}^{M} |p_m(x_i)|^2} \qquad (2)$$

as regularization term on $p = (p_1, \ldots, p_M)$. The joint sparsity-term (2) includes the $\ell^1$-norm of the $\ell^2$-norms $\|p_m(x_i)\|_2^2 \triangleq \sum_{m=1}^{M} |p_m(x_i)|^2$ of the pixel values over all blocks. The inner $\ell^2$-norm couples together the different sound sources that represent the same absorption object in different ones of the photoacoustic responses, whereas the outer $\ell^1$-norm accounts for the required sparsity. By exploiting the joint-support assumption, the $\ell^{2,1}$-term $\|p\|_{2,1}$ has higher super-resolution capacity than the pure $\ell^{21}$-term $\|p\|_1 = \sum_{i=1}^{N} \sum_{m=1}^{M} |p_m(x_i)|$. In some embodiments, the block-FISTA described in this disclosure may realize a joint-sparsity approach.

Figure 2A:
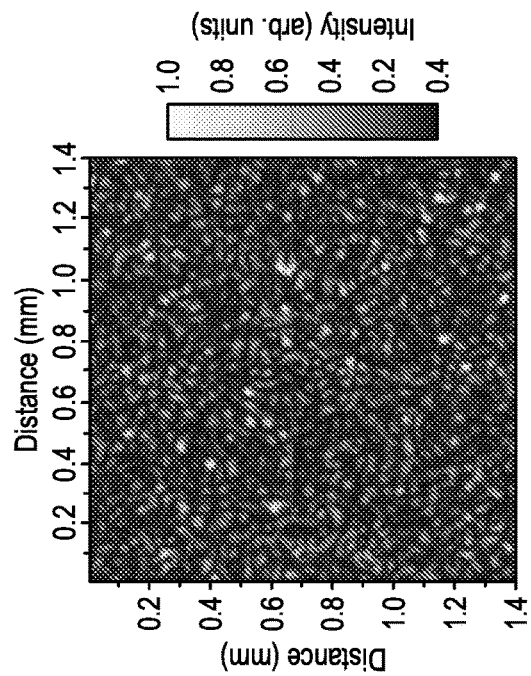
FIG. 2A illustrates an example absorber distribution of an example absorbing object that includes a series of 10 micrometer (μm) wide lines separated by distances varying between 40 μm and 150 μm.
Figure 2B:
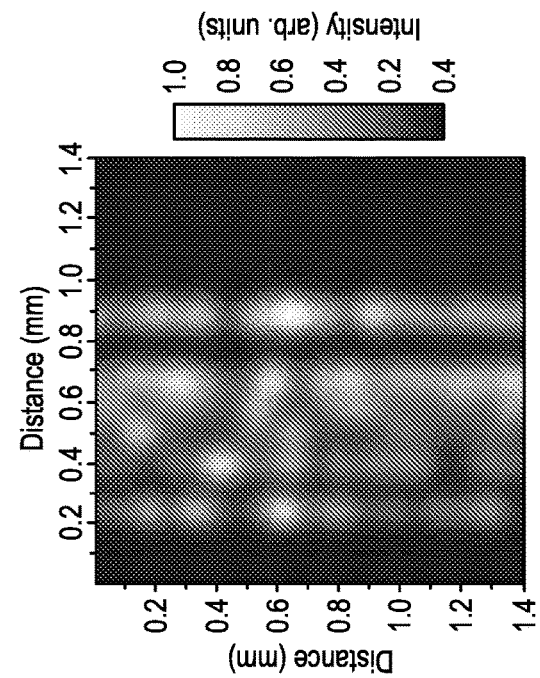
FIG. 2B illustrates a speckle pattern with an example speckle size of 25 μm.
Figure 2C:
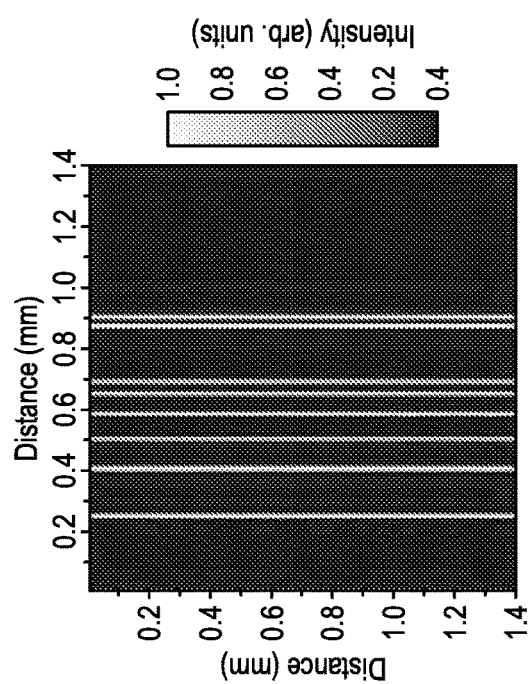
FIG. 2C illustrates a product of the absorber distribution of FIG. 2A and the speckle pattern of FIG. 2B giving a photoacoustic (PA) source distribution.
Figure 2D:
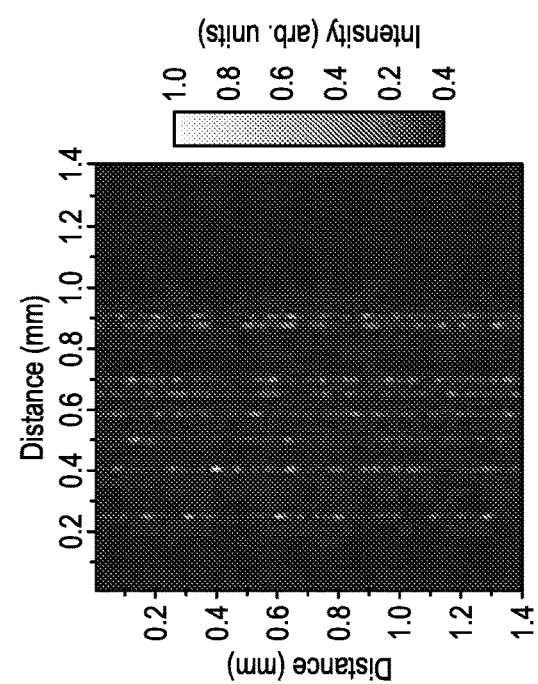
FIG. 2D illustrates a detected PA response found by convolving the PA source distribution of FIG. 2C with a transducer PSF.

In some embodiments, the BSIPAM can be implemented to improve the resolution of photoacoustic imaging. A specific example is described with respect to FIGS. 2A-3B. In more detail, FIG. 2A illustrates an example absorber distribution of an example absorbing object that includes a series of 10 micrometer (μm) wide lines separated by distances varying between 40 μm and 150 μm. FIG. 2B illustrates a speckle pattern with an example speckle size of 25 μm. FIG. 2C illustrates a product of the absorber distribution of FIG. 2A and the speckle pattern of FIG. 2B giving a PA source distribution. FIG. 2D illustrates a detected PA response found by convolving the PA source distribution of FIG. 2C with a transducer PSF.

In the example of FIG. 2A, a simple one-dimensional sample (constant along the vertical axis in FIG. 2A) can be used where the absorber distribution $\rho$ is a set of 8 lines of 10 μm thickness each. The distance between lines varies between 40 and 150 μm. The absorbing object (e.g., the 8 lines) is illuminated with the speckle pattern shown in FIG. 2B where the speckle size is 25 μm. The product of the speckle intensity and absorber distribution gives the spatial distribution of the photoacoustic sources shown in FIG. 2C.

Next, it is assumed that the absorbing object lies in the focal plane of an ultrasonic transducer with a Gaussian PSF h. The Gaussian PSF h may have a full width at half maximum (FWHM) = 100 μm in an example. Scanning the transducer across the imaging plane, the PA response may be found by convolving the source distribution of FIG. 2C with the transducer PSF h, and the result is shown in FIG. 2D, where only lines with the largest separations are clearly resolved.

The experiment may now be repeated M = 100 times or another number of times by applying a new random speckle pattern each time and using the procedure above to calculate the photoacoustic response to a line scan across the absorber distribution (a single horizontal line from FIG. 2D).

Figure 3A:
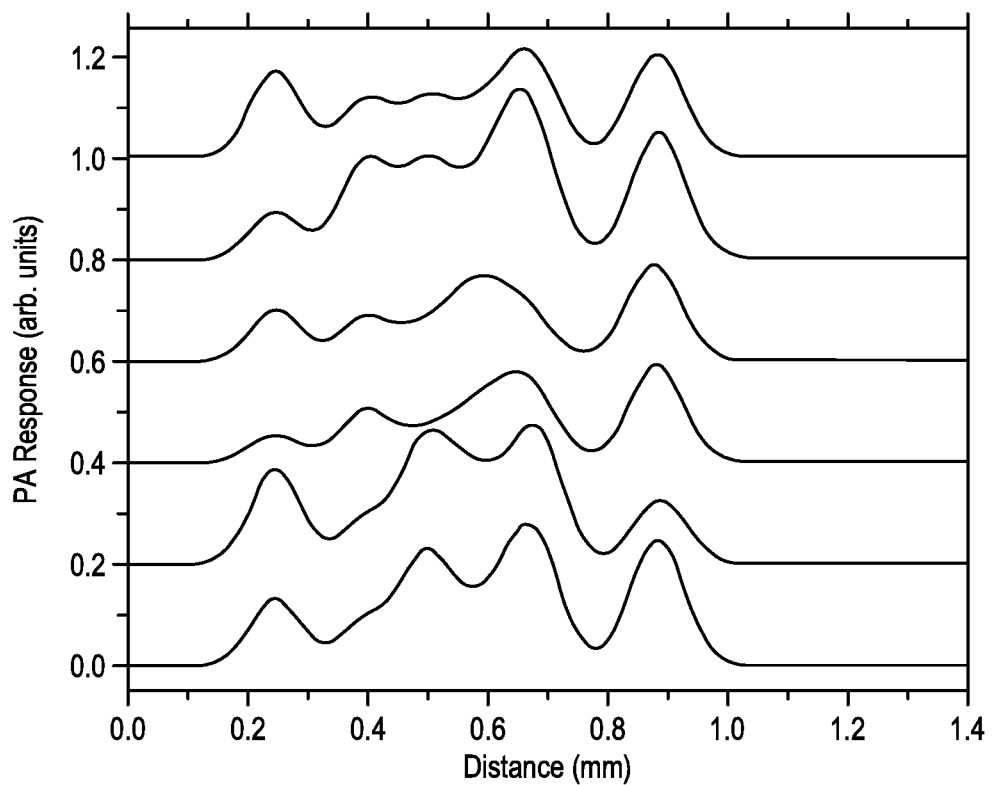
FIG. 3A illustrates six example line scans over the absorber distribution of FIG. 2A, each line scan from a different speckle pattern.

FIG. 3A illustrates six such line scans over the absorber distribution of FIG. 2A, each line scan from a different speckle pattern. It is apparent that the structured illumination patterns, via the random speckle illumination, influence the line scan PA response. It is precisely this variation that may be exploited for super-resolution imaging.

Figure 3B:
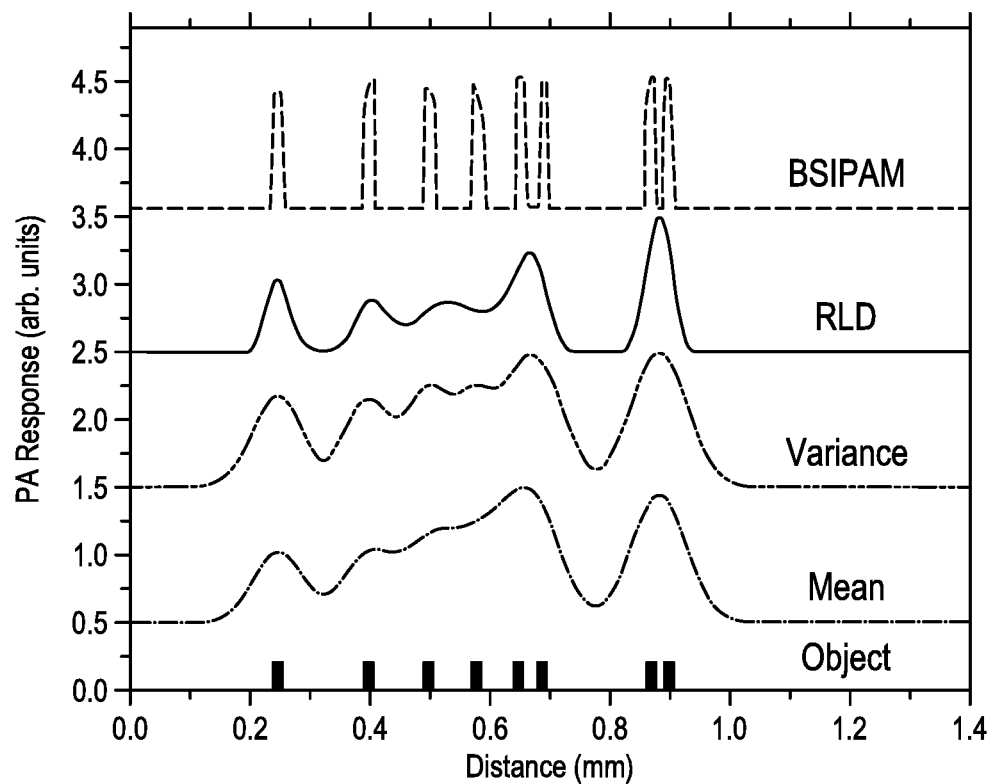
FIG. 3B shows a comparison of several techniques to reconstruct the absorber distribution of FIG. 2A, e.g., using the line scans of FIG. 3A.

FIG. 3B shows a comparison of several techniques to reconstruct the absorber distribution of FIG. 2A, e.g., using the line scans of FIG. 3A. The outputs of each technique are labeled with the name of the technique and include a mean response ("mean" in FIG. 3B), a variance response ("variance" in FIG. 3B), a RLD of the mean response ("RLD" in FIG. 3B), and a BSIPAM response ("BSIPAM" in FIG. 3B). FIG. 3B additionally illustrates the actual absorber distribution ("object" in FIG. 3B).

In all cases, a 10% random noise has been added to the data (e.g., to the line scan PA responses such as those of FIG. 3A) prior to reconstruction. The mean response corresponds to the photoacoustic response obtained through averaging all of the line scan PA responses. The variance may be obtained through plotting the square root of the signal variance at each spatial position. Given a Gaussian PSF, in some embodiments, it can be expected that this may result in a 2½ increase in the spatial resolution over the mean response and the improvement is evident in the simulation of FIG. 3B. The RLD response shows the deconvolution of the mean response given the associated PSF. Finally, the BSIPAM response shows the result obtained through the example block-FISTA algorithm as described herein. Here, even the smallest feature spacing (40 μm) is resolved giving a clear resolution advantage over the other approaches of mean, variance, and RLD.

In some embodiments, reconstruction can exploit the joint sparsity of the sound sources $p_m \triangleq \Phi_m \cdot \rho$ coming from the same density distribution and therefore the supports:

$$\operatorname{supp}(p_m) \triangleq \{i \in \{1, \ldots, N\} \mid p_m(x_i) \neq 0\} \qquad (3)$$

of the sound sources are actually contained in the support of the original density distribution $\rho$. This is implemented by approximating the source distribution by $p^* \triangleq \sum_{m=1}^{M} p_m * \Phi^*$, where $\Phi^* \in \mathbb{R}^N$ is the average speckle intensity (that is allowed to be spatially varying) and $p^* = (p_1^*, \ldots, p_M^*)$ is the minimizer of the unconstrained optimization problem:

$$F(p) = \frac{1}{2} \sum_{m=1}^{M} \sum_{n=1}^{N} |h * p_m(x_i) - y_m(x_i)|^2 + \alpha_1 \|p\|_{2,1} + \frac{\alpha_2}{2} \|p\|_2^2 \to \min \qquad (4)$$

In (4), $\alpha_1$ and $\alpha_2$ may be regularization parameters.

In some embodiments, an additional quadratic penalty term of the form $\|p\|_2^2 \triangleq \sum_{m=1}^{M} \sum_{n=1}^{N} |p_m(x_i)|^2$ that is included in (4) may provide improved stability and/or can avoid numerical solutions being too sparse. In some embodiments, $\frac{1}{2} \sum_{m=1}^{M} \sum_{n=1}^{N} |h * p_m(x_i) - y_m(x_i)|^2$ included in (4) is the so-called data fitting term. In some embodiments, $$\alpha_1 \|p\|_{2,1} + \frac{\alpha_2}{2} \|p\|_2^2$$

included in (4) may be the joint-sparsity inducing regularization term. In some embodiments, the regularization term may be a combination of the block $\ell^1$-penalty $\|p\|_1 = \sum_{i=1}^{N} \sqrt{\sum_{m=1}^{M} |p_m(x_i)|^2}$ which may enforce block-sparsity and the $\ell^2$-penalty $\|p\|_2^2 \ell \sum_{m=1}^{M} \sum_{n=1}^{N} |p_m(x_i)|^2$, which may provide improved stability.

In some embodiments, for example, the extreme case $\alpha 2=0$ corresponds to the use of a pure block-sparsity penalty whereas the choice $\alpha 1=0$ corresponds to the use of a pure quadratic penalty. In a non-block version, the mixture of $\ell^1$- and $\ell^2$-penalty is known as elastic-net regularization.

In some embodiments, the objective to be minimized can be written as the sum $F(p)=f(p)+g_{\alpha_1,\alpha_2}(p)$ of the smooth data fitting term $f(p) \ell \frac{1}{2} \sum_{m=1}^{M} \sum_{n=1}^{N} |h*p_m(x_i)|^2$ and the non-smooth but convex regularization term $$g_{\alpha_1,\alpha_2}(p) = \alpha_1 \|p\|_{2,1} + \frac{\alpha_2}{2} \|p\|_2^2.$$

Any algorithm can be used to solve this equation. In some embodiments, FISTA, also sometimes referred to herein as block-FISTA, may be used. The FISTA alternatively performs a gradient step for the data fitting term and a so-called proximal step for the regularization term. In some embodiments, the proximal step equals the soft-thresholding operation. For a mixed block-sparsity penalty $$g_{\alpha_1,\alpha_2}(p) = \alpha_1 \|p\|_{2,1} + \frac{\alpha_2}{2} \|p\|_2^2,$$

the soft-thresholding operation can be generalized to the block soft-thresholding operation additionally accounting for the quadratic term $\|p\|_2^2$, and can be computed to:

$$[\mathbb{T}_{\alpha_1,\alpha_2}(p)](x_i) = \max\left\{0, 1 - \frac{\alpha_1}{\sqrt{\sum_{m=1}^{M} |p_m(x_i)|^2}}\right\} \frac{p(x_i)}{1+\alpha_2}. \quad (5)$$

In some embodiments, a block-FISTA may include a process 650 shown in FIG. 6B, which is described in more detail below.

Figure 6A:
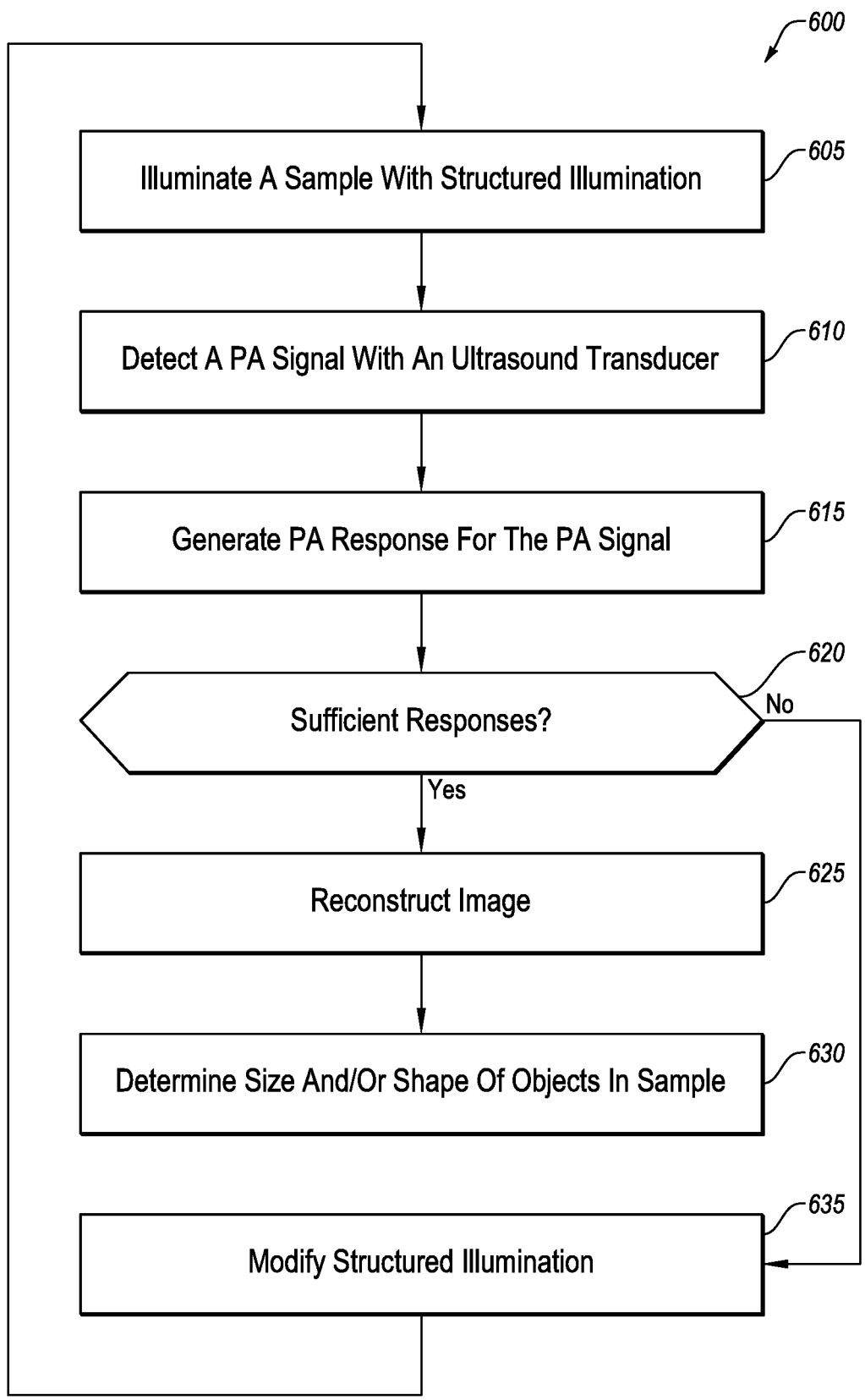
FIG. 6A is a flowchart of an example process for high resolution photoacoustic imaging in scattering media using structured illumination.

FIG. 6A is a flowchart of an example process 600 for high resolution photoacoustic imaging in scattering media using structured illumination. The method 600 may be performed, in whole or in part, by the photoacoustic system 100 of FIG. 1, other photoacoustic systems, a processor or other computer device as in FIG. 8, or other suitable device or system. The process 600 may include one or more of blocks 605, 610, 615, 620, 625, 630, and/or 635.

At block 605, a sample with an absorbing object may be illuminated with structured illumination. At block 610, a PA signal emitted by the absorbing object may be detected with an ultrasound transducer. The ultrasound transducer may include or correspond to an ultrasound transducer described with respect to FIG. 1 or other ultrasound transducer. The physical parameters of the ultrasound transducer determine its LSF and/or PSF.

At block 615, a PA response for the PA signal may be generated. The PA response may be generated, e.g., by an oscilloscope sampling the output of the ultrasound transducer. The oscilloscope may include or correspond to an oscilloscope described with respect to FIG. 1 or other oscilloscope.

At block 620, it may be determined whether a sufficient number of PA responses, each generated responsive to illumination of the sample with different structured illumination (e.g., a different speckle pattern), have been gathered. Determining whether a sufficient number of PA responses have been gathered may include determining whether the number of gathered PA responses exceeds a threshold number, such as 100. Alternatively or additionally, determining whether the gathered number of PA responses is sufficient may be determined in some other manner (e.g., data driven or user specified). Block 620 may be followed by block 635 ("No" at block 620) or by block 625 ("Yes" at block 620).

At block 635, the structured illumination may be modified and the process 600 may return to block 605 where blocks 605, 610, 615, and 620 may be repeated based on the modified structured illumination. Modifying the structured illumination at block 605 may include modifying a speckle pattern of illumination. For instance, modifying the structured illumination may include rotating a diffuser disposed in an optical path between a laser or other light source and the sample to alter a speckle pattern of light that reaches the sample from the light source.

On the other hand, after sufficient PA responses have been gathered at block 620, the process 600 may proceed to block 625. At block 625, an image or absorber distribution may be reconstructed according to the BSIPAM algorithm described herein. Alternatively or additionally, reconstructing the image or absorber distribution at block 625 may include performing a block-FISTA process as described herein. The reconstructed image may have a spatial resolution that far exceeds that of the ultrasound transducer.

At block 630, a size and/or shape of objects in the sample may be determined from the reconstructed image. Alternatively or additionally, a relative orientation and/or location of objects in the sample may be determined from the reconstructed image.

Figure 6B:
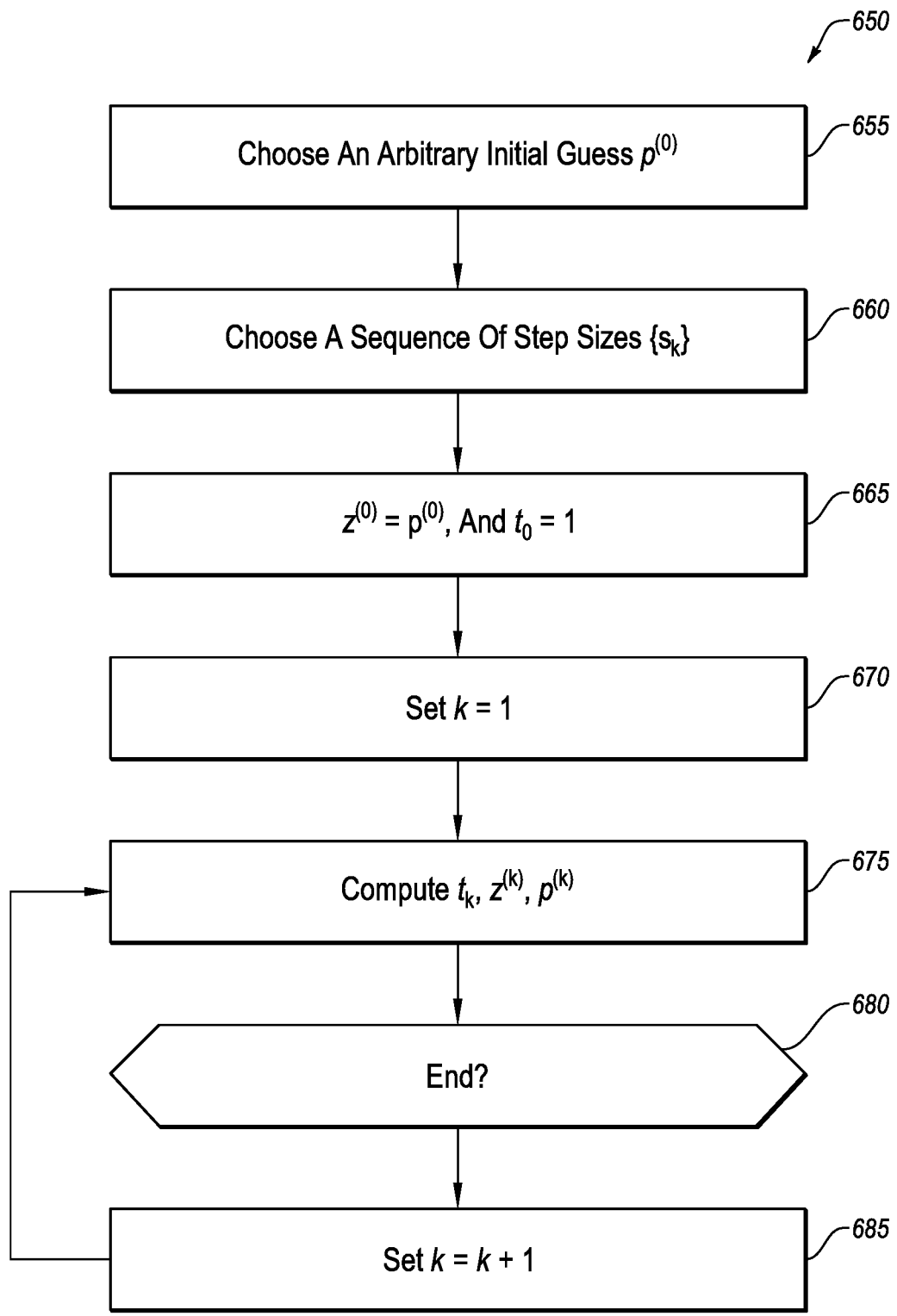
FIG. 6B is a flowchart of an example process of a block-FISTA according to some embodiments.

FIG. 6B is a flowchart of an example process 650 of a block-FISTA process according to some embodiments. In some embodiments, the process 650 may be performed as or within block 625 of the process 600 of FIG. 6A. The process 650 may include one or more of blocks 655, 660, 665, 670, 675, 680, and/or 685. The method 650 may begin at block 655. At block 655, an arbitrary value for p(0) may be chosen. Any value can be chosen. At block 660, a sequence of step sizes, {sk} may be chosen.

At block 665, a few initial values may be determined, for example, $z^{(0)}=p^{(0)}$ and/or $t0=1$. One or more of these initial values may be used subsequently in the process 650, e.g., at block 675 when an increment value k=1. At block 670, the increment value, k, can be set to one, k=1.

At block 675, $t_k$, $z^{(k)}$, and/or $p^{(k)}$ can be calculated, for example, from (6), (7), and/or (8) as follows:

$$p^{(k)} = \mathbb{T}_{s\alpha_1,s\alpha_2}(z^{(k-1)} - s(h*[y_m - h*z_m^{(k-1)}])_{m=1,\ldots,M}) \quad (6)$$

$$t_k = \frac{1+\sqrt{1+4t_{k-1}^2}}{2} \quad (7)$$

$$z^{(k)} = p^{(k)} + \frac{t_{k-1}-1}{t_k}(p^{(k)} - p^{(k-1)}). \quad (8)$$

At block 680, it can be determined whether the algorithm has ended using the gradient of either or both of the smooth data fitting term and the non-smooth but convex regularization term. For example, the process 650 may end if the gradient is below a predetermined threshold value.

In some embodiments, $(h^*[y_m - h^*p_m])_m$ may be the gradient of the data fitting term $f(p)=\frac{1}{2}\sum_{m=1}^{M}\sum_{n=1}^{N}|h^*p_m(x_i)|^2$, which may be repeatedly computed during the iteration at the auxiliary variable $z^{(k)}$, and/or for a step size s>0. Evaluating the gradient steps at) $z^{(k)}$ instead of at $p^{(k)}$ may significantly accelerate the block-FISTA compared to standard gradient algorithms.

In some embodiments, proximal mapping $\mathbb{T}_{s\alpha_1, s\alpha_2}$ may be applied with the parameters $s\alpha_1$ and $s\alpha_2$. The step size may satisfy 0<s≤1/L, where L is the largest Lipschitz constant of the data fitting term, that can be computed to L=2π max{$\hat{h}$(w)}, where $\hat{h}$(w) is the Fourier transform of the convolution kernel h. The Block-FISTA may have, for example, an improved convergence rate of $\mathcal{O}(1/k^2)$ in the function values of $f(\rho)+g_\alpha(\rho)$ compared to the linear convergence rate $\mathcal{O}(1/k)$ of standard gradient algorithms.

If the algorithm has not ended as determined at block 680, then process 650 proceeds to block 685 where k is incremented: k=k+1 and the process 650 then returns to block 675. If the algorithm has ended as determined at block 680, the process 650 ends.

In some embodiments, the block-FISTA reconstruction strategy may be directly applicable to two-dimensional image reconstruction as well. An example of two-dimensional image reconstruction is described below.

To investigate the capabilities of the block-FISTA algorithm (e.g., shown in FIG. 6B) for two dimensional image reconstruction, a star-shaped absorber may be considered that may include several lines. For instance, FIG. 4A illustrates an example absorber distribution of an example star-shaped absorbing object that includes 12 lines arranged in a star pattern, e.g., all the lines emanate radially outward from the perimeter of a circle. FIG. 4B illustrates a simulated mean image of the absorbing object of FIG. 4A, e.g., generated by averaging simulated PA responses generated in response to simulated illumination of the absorbing object with multiple different simulated speckle patterns. FIG. 4C illustrates a simulated deconvolution image of the absorbing object of FIG. 4A, e.g., generated by applying regularized deconvolution to the simulated mean image of FIG. 4B. FIG. 4D illustrates a simulated BSIPAM image of the absorbing object of FIG. 4A, e.g., generated by applying the block-FISTA algorithm (FIG. 6B) to the simulated PA responses generated in response to simulated illumination of the absorbing object with multiple different simulated speckle patterns.

In the example of FIGS. 4A-4D, a sample of size 256 µm² may be used where the closest distance between adjacent lines, e.g., at the perimeter of the circle from which the lines radially emanate, is 17 µm. A PSF of an ultrasound transducer in this example has been taken as a two-dimensional Gaussian kernel with a FWHM of 35 µm. In the mean image of FIG. 4B, the individual lines clearly cannot be separated. The resolution, for example, can be defined as the distance where two lines are clearly separated. According to this definition, the resolution in the mean image of FIG. 4B may be close to 42 µm. Also after applying a (regularized) deconvolution as in FIG. 4B, the lines cannot be separated, although the resolution in FIG. 4C may be increased by a factor 1.4 compared to FIG. 4B. In order to further increase the resolution, the block FISTA algorithm as described herein can be applied; for example, M=200 random speckle patterns can be performed with a speckle size of 9 µm. In some embodiments, the block-FISTA algorithm may separate the lines having a minimal distance of 17 µm. In some embodiments, the block-FISTA algorithm may increase resolution by at least a factor 2.4, e.g., compared to a mean response or image such as the mean image of FIG. 4B.

An experimental validation of the proposed approach will now be described with respect to FIG. 1, which is a schematic of an example photoacoustic system 100 for high resolution photoacoustic imaging in scattering media using structured illumination. The photoacoustic system 100 may include a laser 102, a diffuser 104, an aperture 106, a lens 108, a test tank 110, a translation stage 112, an ultrasound transducer 114, a photodetector 116, an oscilloscope 118, and a sample 120. Alternatively or additionally, the photoacoustic system 100 may include or be communicatively coupled to a processor or other computer device such as described with respect to FIG. 8.

The sample 120 may be placed in the test tank 110, which may have transparent walls and may be filled with water. The laser 102 may include a pulsed, frequency doubled Nd:YAG laser, e.g., with a central emission wavelength λ=532 nm. In other embodiments, the laser 102 may have other implementations and/or may have a different central emission wavelength.

The diffuser 104, the aperture 106, and the lens 108 may be disposed in an optical path between the laser 102 and the sample 120. The diffuser 104, the aperture 106, and the lens 108 may collectively form an optical train configured to focus light from the laser 102 or other light source as structured illumination onto the sample 120.

Alternatively or additionally, the optical train may include a dynamic scattering media, such as biological tissue, instead of or in addition to the diffuser 104. When light propagates through biological tissue, it may generate a speckle pattern. This speckle pattern may change rapidly due to physiological motion. Thus, the diffuser 104 may be omitted in some embodiments or used together with biological tissue, instead or in addition relying on the speckle patterns that may be generated from passing the output of the laser 102 through biological tissue.

The diffuser 104 may include a ground glass diffuser or other component configured to output speckled illumination patterns from input light, e.g., from the laser 102.

An illumination beam 122 emitted by the laser 102 is sent through the diffuser 104 and focused onto the sample 120 using the lens 108. In this experimental setup, the lens 108 has a focal length f=50 mm. In other embodiments, the lens 108 may have a different focal length.

A diameter of the illumination beam 122 diameter may be set by the aperture 106, which may have an adjustable diameter and may be disposed adjacent to the lens 108. A speckle size of the speckled illumination at the focal plane of the lens 108, for example, can be estimated as 1.22λ f/d, where λ is the center wavelength of the illumination beam 122 and d is the aperture 106 diameter.

The ultrasonic transducer 114 may be focused and may record ultrasonic signals, e.g., emitted by the sample 120 responsive to illumination by the speckled illumination. The ultrasonic transducer 114 may include a single ultrasound transducer or an ultrasound transducer array such as those used in medical ultrasound imaging systems. In this experimental setup, the ultrasonic transducer 114 includes a Panametrics V3512 ultrasonic transducer operated at a central frequency of 90 megahertz (MHz) with an element size of 6 millimeters (mm) and a focal length of 13 mm connected to an ultrasonic pulser/receiver implemented as a Panametrics 5073PR with a −3 decibel (dB) bandwidth in a range from 1 kilohertz (kHz)-75 MHz). In other embodiments, the ultrasonic transducer 114 may have other implementations.

The output of the ultrasonic transducer 114 may be sampled by the oscilloscope 118, which in this experimental setup includes a Lecroy HDO6104 12-bit digital oscilloscope. In other embodiments, the oscilloscope 118 may have other implementations.

The photodetector 116 may include a silicon photodetector or other suitable photodetector. The photodetector 116 may be used to sample the pulses of the illumination beam 122 to correct photoacoustic signal amplitudes for shot-to-shot (or pulse-to-pulse) variations in the intensity of the illumination beam 122.

The photodetector 116 may also be used to trigger the oscilloscope 118. For instance, each time the photodetector 116 detects a pulse of the illumination beam 122, the photodetector 116 may trigger the oscilloscope 118 to sample the ultrasound transducer 114 throughout at least a period of time during which the sample 120 is expected to exhibit a PA response in response to illumination with the pulse of the illumination beam 122. This may limit the amount of data generated by the oscilloscope 118 primarily to relevant periods of time. The ultrasonic transducer 114 may be mounted on the translation stage 112. The translation stage 112 may include one or more motorized and/or manual scanning stages. For instance, the translation stage 112 may include a motorized or manual linear scanning stage which moves the transducer in an arbitrarily-defined y-direction depicted in FIG. 1 which is perpendicular to the illumination direction of the illumination beam 122 in FIG. 1 and is general a lateral direction. The translation stage 122 may alternatively or additionally include a motorized or manual linear stage in an arbitrarily-defined z-direction depicted in FIG. 1, which may be used for adjusting a distance between the sample 120 and the ultrasonic transducer 114. Alternatively or additionally, a second motorized or manual linear scanning stage may be used to rotate the diffuser 104 via a v-belt or otherwise adjust the diffuser 104 to alter a speckle pattern that results from the illumination beam 122 passing through the diffuser 104.

Photoacoustic signals, for example, may be acquired with a spatial step size of 10 μm over a total scan length of 1.0 mm. In other embodiments, a different spatial step size and/or a different total scan length may be implemented. Measured time traces were processed in this experimental setup using a Fourier Transform and magnitude spectra were summed between 15 and 85 MHz to get a net photoacoustic response at each spatial location. Using this processing approach, the photoacoustic system 100 in this experimental setup was first characterized by scanning over a single Alpaca fiber as an absorbing object in the sample 120, the Alpaca fiber having a diameter in the 18-25 μm range. In order to avoid speckle artifacts, the measurement was repeated 17 times at different diffuser 104 positions and the results were averaged, e.g., to generate a mean response, to simulate plane wave optical illumination. The mean response was then deconvolved with a step function (25 μm width) approximating the hair to yield the LSF shown in FIG. 5A. The LSF determined in this manner has a FWHM of approximately 110 μm.

In this experimental setup, a sample was fabricated with five Alpaca fibers to use as the absorbing object in the sample 120, as indicated by an inset 124 in FIG. 1. In the inset 124 of FIG. 1, a vertical dashed line indicates an approximate measurement location.

Figure 5A:
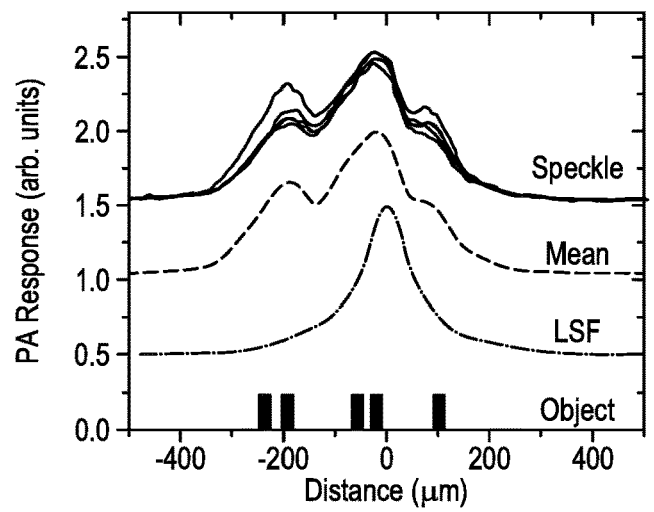
FIG. 5A shows relative locations of a fiber array of FIG. 1, a mean PA response from multiple scans across a sample that includes the fiber array, a subset of the multiple scans, and a LSF of the transducer of FIG. 1

FIG. 5A shows relative locations of the fiber array of FIG. 1, a mean PA response from multiple scans, a subset of the multiple scans, and a LSF of the ultrasound transducer 114 of FIG. 1. In more detail, relative locations of the five fibers in the sample 120 with respect to each other at the ultrasound scan location (based on an optical image), e.g., the absorber distribution, is denoted as the "object" in FIG. 5A. In some embodiments, the absolute position of the fiber array is only an estimate. With combined reference to FIGS. 1 and 5A, the aperture 106 diameter was set to 3.0 mm to yield a speckle size of approximately 10 μm. In this configuration, 101 scans across the fiber array were acquired. The diffuser 104 was rotated after each scan, for example, to provide a unique speckle pattern for each scan. A mean photoacoustic response from all scans, simulating uniform illumination, is shown in FIG. 5A and denoted "mean" in FIG. 5A, along with five individual scans acquired with different speckle patterns which are collectively denoted "speckle" in FIG. 5A. It can be seen at least from the five individual scans of FIG. 5A that the weighting between individual features changes in response to the structured illumination associated with each scan.

Figure 5B:
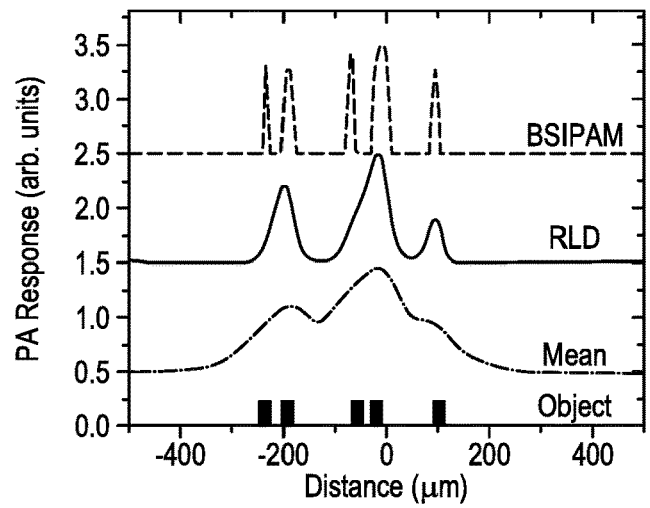
FIG. 5B shows a comparison of several techniques to reconstruct an absorber distribution of the fiber array of FIGS. 1 and 5A based on experimental measurements.

FIG. 5B shows a comparison of several techniques to reconstruct the absorber distribution of the fiber array of FIGS. 1 and 5A based on experimental measurements, e.g., using the line scans discussed with respect to FIGS. 1 and 5A. The outputs of each technique are labeled with the name of the technique and include the mean response of FIG. 5A (also labeled "mean" in FIG. 5B), a RLD of the mean response ("RLD" in FIG. 5B), and a BSIPAM response ("BSIPAM" in FIG. 5B). FIG. 5B additionally illustrates the absorber distribution (also labeled "object" in FIG. 5B).

In the example of FIG. 5B, the BSIPAM technique as described herein is the only technique able to clearly resolve all five fibers, and the relative positions of the fibers in the reconstructed BSIPAM response agrees well with that measured using optical microscopy, e.g., the absorber distribution labeled "object" in FIG. 5B. Given the measured LSF for the ultrasound transducer 114, one can just begin to resolve two lines in the mean response when the line spacing reaches approximately 80 μm. The minimum fiber spacing, resolved using BSIPAM, may be estimated to be less than 40 μm giving a resolution enhancement of at least two.

FIG. 5A shows relative locations of the fiber array of FIG. 1, a mean PA response from multiple scans, a subset of the multiple scans, and a LSF of the ultrasound transducer 114 of FIG. 1

Figure 5C:
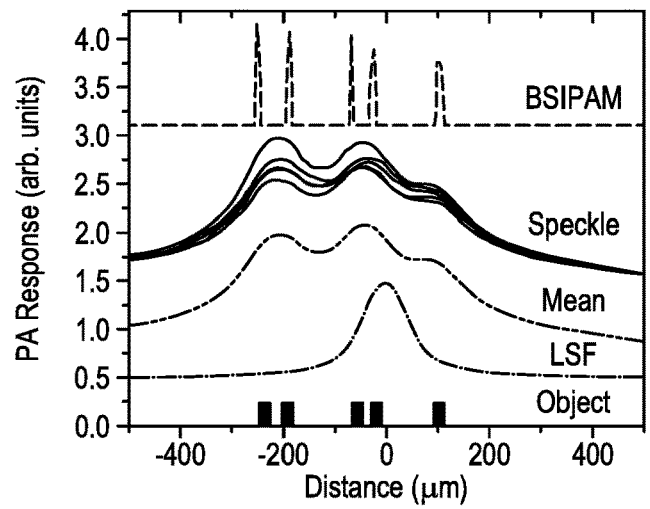
FIG. 5C shows relative locations of a simulated fiber array, a simulated mean PA response from multiple simulated scans, a subset of the multiple simulated scans, a simulated LSF of a simulated ultrasound transducer, and a simulated BSIPAM response.

FIG. 5C shows relative locations of a simulated fiber array, a simulated mean PA response from multiple simulated scans, a subset of the multiple simulated scans, a simulated LSF of a simulated ultrasound transducer, and a simulated BSIPAM response. In this example, the simulated fiber array includes 18 μm fibers with the fiber spacing matching that from the optical image of FIGS. 5A and 5B, all labeled "object" in the corresponding Figure. The transducer LSF is calculated for a broadband transducer with a 40 MHz central frequency and a FWHM of 110 μm. A 10% random noise has been added to the data prior to reconstruction, and the speckle size was set to 10 μm. 100 line scans with different speckle patterns were simulated, and the individual line scans, collectively labeled "speckle" in FIG. 5C, again show fluctuations indicative of the random speckle illumination. The BSIPAM approach allows for resolution of all five lines in agreement with what was found experimentally. In some embodiments, BSIPAM can utilize the fact that the photoacoustic signals generated by different random speckle patterns are indeed different.

In some embodiments, if structural information is scrambled by diffusive or dissipative phenomena, like scattering, absorption, or diffusion, joint sparsity (e.g., block sparsity) can be used to gain better spatial resolution from blind structured illumination measurements. In some embodiments, a gain in resolution of more than a factor of two has been achieved experimentally in one-dimensional PA imaging, and numerically also in two dimensions, using multiple speckle illuminations and the techniques described herein. The differences in the photoacoustic signals generated with random speckle patterns are utilized in BSIPAM using the block-FISTA reconstruction algorithm. This algorithm reconstructs the absorbing structure from measured PA signals with a resolution close to the speckle size and has the potential for reconstructing structural information from signals measured with other modalities using blind structured illumination, like photothermal imaging or lateral structures in optical coherence tomography.

Figure 7:
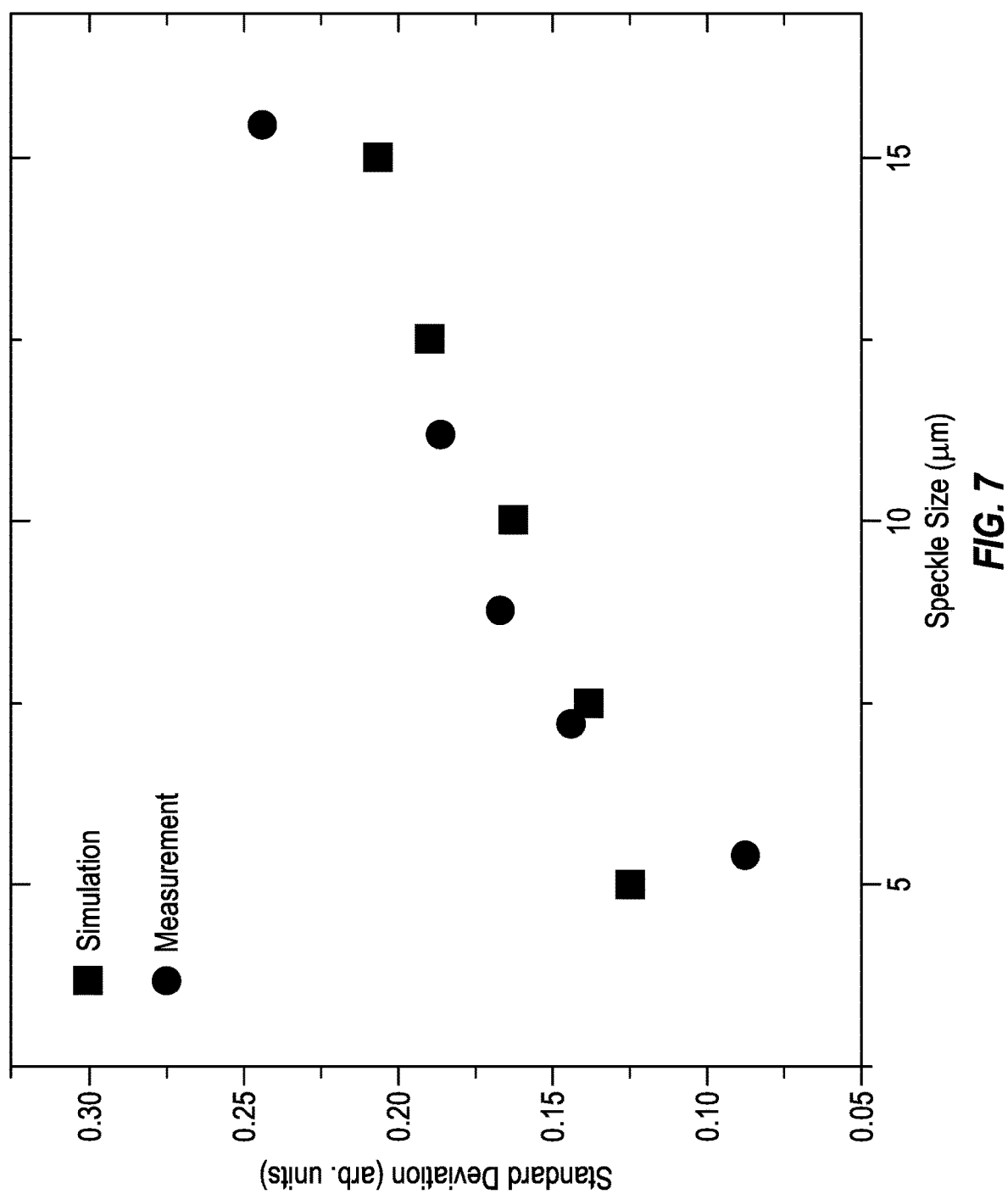
FIG. 7 is a graph showing both simulated and experimentally measured standard deviation of PA responses as a function of speckle size.

FIG. 7 is a graph that illustrates both simulated and experimentally measured standard deviation of PA responses as a function of speckle size. The experimentally measured standard deviation of the PA responses were based on measurements with a transducer focused on a single fiber. The simulated results of FIG. 7 were calculated using an 18 mm wide fiber with the LSF shown in FIG. 5C. The calculated and measured data sets at each speckle size were normalized such that the mean PA signal amplitude was one.

In a specific example, the transducer was positioned over a single Alpaca fiber as an absorbing object in a sample to be measured and the photoacoustic signal was measured for 201 distinct speckle patterns, and this process was repeated for five different speckle sizes as controlled by aperture diameter. Using the various procedures described in this disclosure, each signal was processed to obtain the photoacoustic response and the responses at each speckle size were normalized such that the mean response was unity. The standard deviation of the normalized responses as a function of speckle size is shown in FIG. 7. As expected, there is an increase in signal variation as the speckle size increases. In some embodiments, the resolution of BSIPAM may be dictated by the ability of the detection system to distinguish subtle changes in the photoacoustic response at small speckle sizes. Also shown in FIG. 7 is standard deviation found from the simulated photoacoustic response using the same parameters used for FIG. 5C but with a single Alpaca fiber.

Figure 8:
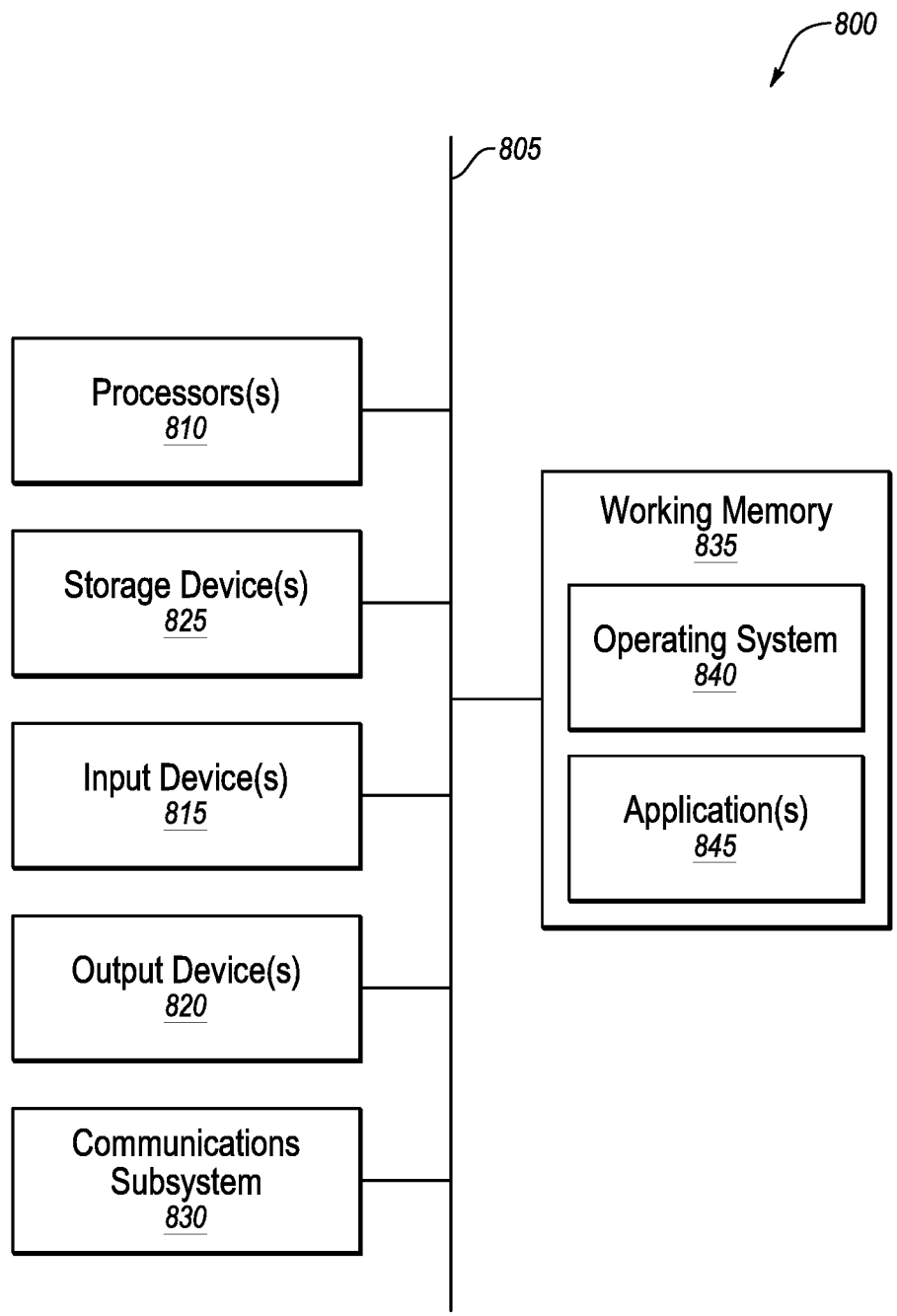
FIG. 8 shows an illustrative computational system for performing functionality to facilitate implementation of embodiments described herein.

The various flowcharts, processes, computers, servers, the solving of equations, etc. described in this document may be executed in part, for example, using the computational system 800 (or processing unit) illustrated in FIG. 8. For example, the computational system 800 can be used alone or in conjunction with other components. As another example, the computational system 800 can be used to perform any calculation, solve any equation, perform any identification, and/or make any determination described here.

The computational system 800 may include any or all of the hardware elements shown in the figure and described herein. The computational system 800 may include hardware elements that can be electrically coupled via a bus 805 (or may otherwise be in communication, as appropriate). The hardware elements can include one or more processors 810, including, without limitation, one or more general-purpose processors and/or one or more special-purpose processors (such as digital signal processing chips, graphics acceleration chips, and/or the like); one or more input devices 815, which can include, without limitation, a mouse, a keyboard, and/or the like; and one or more output devices 820, which can include, without limitation, a display device, a printer, and/or the like.

The computational system 800 may further include (and/or be in communication with) one or more storage devices 825, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The computational system 800 might also include a communications subsystem 830, which can include, without limitation, a modem, a network card (wireless or wired), an infrared communication device, a wireless communication device, and/or chipset (such as a Bluetooth® device, a 802.6 device, a Wi-Fi device, a WiMAX device, cellular communication facilities, etc.), and/or the like. The communications subsystem 830 may permit data to be exchanged with a network (such as the network described below, to name one example) and/or any other devices described herein. In many embodiments, the computational system 800 will further include a working memory 835, which can include a RAM or ROM device, as described above.

The computational system 800 also can include software elements, shown as being currently located within the working memory 835, including an operating system 840 and/or other code, such as one or more application programs 845, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 825 described above.

In some cases, the storage medium might be incorporated within the computational system 800 or in communication with the computational system 800. In other embodiments, the storage medium might be separate from the computational system 800 (e.g., a removable medium, such as a compact disc, etc.), and/or provided in an installation package, such that the storage medium can be used to program a general-purpose computer with the instructions/code stored thereon. These instructions might take the form of executable code, which is executable by the computational system 800 and/or might take the form of source and/or installable code, which, upon compilation and/or installation on the computational system 800 (e.g., using any of a variety of generally available compilers, installation programs, compression/decompression utilities, etc.), then takes the form of executable code.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device. Embodiments of the methods disclosed herein may be performed in the operation of such computing devices. The order of the blocks presented in the examples above can be varied for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps.

Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

What is claimed is:

1. A method for high resolution photoacoustic imaging in scattering media using structured illumination, the method comprising:
   illuminating a sample of an absorption object with structured illumination, including illuminating the sample with a plurality of different speckle patterns at different times;
   detecting a plurality of photoacoustic signals generated by the absorption object in response to illumination with the plurality of different speckle patterns to generate a plurality of photoacoustic responses; and
   reconstructing an absorber distribution of the absorption object by exploiting joint sparsity of sound sources in the plurality of photoacoustic responses.

2. The method of claim 1, reconstructing the absorber distribution of the absorption object by exploiting joint sparsity of sound sources in the plurality of photoacoustic responses comprises minimizing a sum of a smooth data fitting term f(p) and a non-smooth but convex regularization term $g_{\alpha_1,\alpha_2}(p)$.

3. The method of claim 2, wherein:
   the smooth data fitting term f(p) depends on a point spread function (PSF) or a line spread function (LSF) of an ultrasound transducer that detects the plurality of photoacoustic signals and on the sound sources in the plurality of photoacoustic responses;
   the convex regularization term $g_{\alpha_1,\alpha_2}(p)$ depends on an $\ell^1$-norm and $\ell^2$-norms of pixel values over all blocks;
   the $\ell^1$-norm accounts for sparsity; and
   an inner one of the $\ell^2$-norms couples together different sound sources that represent the same absorption object in different ones of the plurality of photoacoustic responses.

4. The method of claim 2, wherein minimizing the sum of the smooth data fitting term f(p) and the non-smooth but convex regularization term $g_{\alpha_1,\alpha_2}(p)$ comprises minimizing the sum of the smooth data fitting term $f(p) \triangleq \sum_{m=1}^{M} \sum_{n=1}^{N} (|h * p_m(x_i)|^2$ and the non-smooth but convex regularization term $$g_{\alpha_1,\alpha_2}(p) = \alpha_1 \|p\|_{2,1} + \frac{\alpha_2}{2}\|p\|_2^2.$$

5. The method of claim 4, wherein M is a number of the plurality of photoacoustic responses, N is a number of data points that make up each of the plurality of photoacoustic responses, h is a point spread function (PSF) or a line spread function (LSF) of an ultrasound transducer that detects the plurality of photoacoustic signals, and $p_m(x_i)$ is a sound source in an mth one of the plurality of photoacoustic responses at each data point $x_i$.

6. The method of claim 2, wherein minimizing the sum of the smooth data fitting term f(p) and the non-smooth but convex regularization term $g_{\alpha_1,\alpha_2}(p)$ comprises minimizing the sum of the smooth data fitting term f(p) and the non-smooth but convex regularization term $g_{\alpha_1,\alpha_2}(p)$ using a block-fast iterative threshold algorithm (FISTA).

7. The method of claim 6, wherein minimizing the sum of the smooth data fitting term f(p) and the non-smooth but convex regularization term $g_{\alpha_1,\alpha_2}(p)$ using the block-FISTA includes performing a gradient step for the smooth data fitting term f(p) and performing a proximal step for the non-smooth but convex regularization term $g_{\alpha_1,\alpha_2}(p)$.

8. The method of claim 7, wherein performing the proximal step comprises performing a soft-thresholding operation.

9. The method of claim 6, wherein minimizing the sum of the smooth data fitting term f(p) and the non-smooth but convex regularization term $g_{\alpha_1,\alpha_2}(p)$ using the block-FISTA includes:
- determining an arbitrary value $p^{(0)}$ for the absorber distribution $p^{(k)}$;
- selecting a sequence of step sizes $\{s_k\}$;
- determining initial values $z^{(0)} = p^{(0)}$ and $t_0 = 1$;
- setting an integer increment value, k, to k=1; and
- calculating $t_k$, $z^{(k)}$, and/or $p^{(k)}$ according to:

$$p^{(k)} = \mathbb{T}_{s\alpha_1, s\alpha_2}(z^{(k-1)} - s(h * [y_m - h * z_m^{(k-1)}])_{m=1,\ldots,M}),$$

$$t_k = \frac{1 + \sqrt{1 + 4t_{k-1}^2}}{2}, \text{ and}$$

$$z^{(k)} = p^{(k)} + \frac{t_{k-1} - 1}{t_k}(p^{(k)} - p^{(k-1)}), \text{ where}$$

$$[\mathbb{T}_{s\alpha_1, s\alpha_2}(p)](x_i) = \max\left\{0, 1 - \frac{\alpha_1}{\sqrt{\sum_{m=1}^{M} |p_m(x_i)|^2}}\right\} \frac{p(x_i)}{1 + \alpha_2}$$

denotes a block-soft thresholding operation.

10. A non-transitory computer-readable medium having computer-readable instructions stored thereon that are executable by a processor to perform the method of claim 1.

11. An apparatus, comprising:
- a light source;
- an optical train configured to focus light from the light source as structured illumination onto a sample that includes an absorption object, wherein the structured light includes a plurality of different speckle patterns focused on the sample at a plurality of different times;
- an ultrasound transducer configured to generate a plurality of photoacoustic responses of a plurality of photoacoustic signals generated by the absorption object in response to illumination with the plurality of different speckle patterns, the ultrasound transducer having a point spread function (PSF) or a line spread function (LSF); and
- a processor configured to perform operations comprising reconstructing an absorber distribution of the absorption object by exploiting joint sparsity of sound sources in the plurality of photoacoustic responses using the PSF or LSF of the ultrasound transducer.

12. The apparatus of claim 11, wherein the ultrasound transducer consists essentially of a single ultrasound transducer.

13. The apparatus of claim 11, wherein the ultrasound transducer comprises an ultrasound transducer array.

14. The apparatus of claim 11, wherein the light source is configured to emit pulses of an illumination beam toward the sample, each pulse that reaches the sample having a different speckle pattern than other pulses.

15. The apparatus of claim 14, wherein the optical train comprises a diffuser located in an optical path between the light source and the sample.

16. The apparatus of claim 15, further comprising a motorized scanning stage configured to rotate the diffuser about an axis parallel to a direction of travel of the light through the diffuser between an end of one pulse and a beginning of a next pulse to modify the structured illumination to have a different speckle pattern at the sample from one pulse to the next.

17. The apparatus of claim 16, wherein the optical train further comprises:
- an adjustable aperture located in the optical path between the diffuser and the sample; and
- a lens located in the optical path between the adjustable aperture and the sample,
- wherein a speckle size of the plurality of different speckle patterns of the structured illumination depends on a center wavelength of the light, a focal length of the lens, and a diameter of the adjustable aperture.

18. The apparatus of claim 17, wherein a spatial resolution of the absorber distribution is within a range of one to two times the speckle size.

19. The apparatus of claim 17, wherein a spatial resolution of the absorber distribution is limited by the speckle size rather than the LSF or PSF of the ultrasound transducer.

20. The apparatus of claim 11, wherein reconstructing the absorber distribution of the absorption object by exploiting joint sparsity of sound sources in the plurality of photoacoustic responses comprises minimizing a sum of a smooth data fitting term f(p) and a non-smooth but convex regularization term $g_{\alpha_1,\alpha_2}(p)$.

21. The apparatus of claim 20, wherein minimizing the sum of the smooth data fitting term f(p) and the non-smooth but convex regularization term $g_{\alpha_1,\alpha_2}(p)$ comprises minimizing the sum of the smooth data fitting term f(p) and the non-smooth but convex regularization term $g_{\alpha_1,\alpha_2}(p)$ using a block-fast iterative threshold algorithm (block-FISTA).

22. The apparatus of claim 21, wherein minimizing the sum of the smooth data fitting term f(p) and the non-smooth but convex regularization term $g_{\alpha_1,\alpha_2}(p)$ using the block-FISTA includes performing a gradient step for the smooth data fitting term f(p) and performing a proximal step for the non-smooth but convex regularization term $g_{\alpha_1,\alpha_2}(p)$.

* * * * *